United States Patent
Lin et al.

(10) Patent No.: US 9,678,009 B2
(45) Date of Patent: Jun. 13, 2017

(54) METHOD FOR LOCALIZED SURFACE PLASMON RESONANCE SENSING SYSTEM

(71) Applicant: NATIONAL CHENG KUNG UNIVERSITY, Tainan (TW)

(72) Inventors: Chun-Hung Lin, Tainan (TW); Wen-Yu Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 14/877,944

(22) Filed: Oct. 8, 2015

(65) Prior Publication Data

US 2016/0033402 A1 Feb. 4, 2016

Related U.S. Application Data

(63) Continuation of application No. 14/080,953, filed on Nov. 15, 2013.

(30) Foreign Application Priority Data

May 30, 2013 (TW) .............................. 102119090 A

(51) Int. Cl.
*G01J 4/00* (2006.01)
*G01N 21/552* (2014.01)

(52) U.S. Cl.
CPC ......... *G01N 21/553* (2013.01); *G01N 21/554* (2013.01)

(58) Field of Classification Search
CPC .................. G01N 21/554; G01N 21/21; G01N 33/54373; B82Y 15/00

(Continued)

(56) References Cited

U.S. PATENT DOCUMENTS

2004/0142482 A1 7/2004 Westphal
2006/0141466 A1* 6/2006 Pinet ...................... G01N 21/23
435/6.11

(Continued)

FOREIGN PATENT DOCUMENTS

JP 2000-121551 A 4/2000
TW 200724901 7/2007

(Continued)

OTHER PUBLICATIONS

Offermans et al., "Universal Scaling of the Figure of Merit of Plasmonic Sensors", ACS Nano, 2011, vol. 5, No. 6, pp. 5151-5157.

(Continued)

*Primary Examiner* — Tarifur Chowdhury
*Assistant Examiner* — Sunghee Y Gray
(74) *Attorney, Agent, or Firm* — CKC & Partners Co., Ltd.

(57) ABSTRACT

A method for a localized surface plasmon resonance (LSPR) sensing system is disclosed. The LSPR sensing system has an optical detection system and a test specimen with metal nanoparticles arranged in an anisotropic periodic manner that generates a phase signal of the LSPR sensing system. The method includes: emitting an incident light toward the test specimen to excite the metal nanoparticles, thereby generating an emergent light; using the optical detection system to detect phases of a first polarization state and a second polarization state of the emergent light, where the first polarization state is perpendicular to the second polarization state; and obtaining a phase difference spectrum between the phases of the first and second polarization states, thereby determining a half maximum (FWHM) of the phase difference spectrum.

15 Claims, 9 Drawing Sheets

(58) Field of Classification Search
USPC .......................................................... 356/369
See application file for complete search history.

(56) References Cited

U.S. PATENT DOCUMENTS

| | | |
|---|---|---|
| 2008/0019876 A1 | 1/2008 | Chau et al. |
| 2008/0160287 A1 | 7/2008 | Misawa et al. |
| 2008/0213130 A1* | 9/2008 | Pison ..................... B82Y 5/00 422/68.1 |
| 2009/0002701 A1 | 1/2009 | Fattal et al. |
| 2010/0171958 A1 | 7/2010 | Chau et al. |
| 2010/0178713 A1 | 7/2010 | Nishiuma et al. |
| 2010/0220328 A1* | 9/2010 | Isaka ................... G01N 21/554 356/445 |
| 2010/0233825 A1 | 9/2010 | Yamada et al. |
| 2010/0259754 A1 | 10/2010 | Hooper et al. |
| 2011/0013192 A1 | 1/2011 | Yang et al. |
| 2011/0205542 A1 | 8/2011 | Pendell Jones et al. |
| 2011/0216320 A1 | 9/2011 | Cho et al. |
| 2012/0069336 A1 | 3/2012 | Rakitzis |
| 2013/0092823 A1 | 4/2013 | Amako et al. |
| 2013/0329272 A1 | 12/2013 | Matsumura et al. |

FOREIGN PATENT DOCUMENTS

| | | |
|---|---|---|
| TW | 201027065 A | 7/2010 |
| TW | 201104237 A | 2/2011 |
| TW | 201250229 A | 12/2012 |

OTHER PUBLICATIONS

Communication From the Patent Office of Taiwan Regarding a Counterpart Foreign Application Dated (Taiwan Year 103) Nov. 20, 2014.

* cited by examiner

METHOD FOR LOCALIZED SURFACE PLASMON RESONANCE SENSING SYSTEM

RELATED APPLICATIONS

This application is a continuation application of the U.S. application Ser. No. 14/080,953, filed on Nov. 15, 2013, which claims the priority benefit of Taiwan Application Serial Number 102119090, filed on May 30, 2013. All disclosures are incorporated herewith by reference.

BACKGROUND

Field of the Invention

The present invention relates to a localized surface plasmon resonance (LSPR) sensing system with particles arranged in an anisotropic period, especially to a LSPR sensing system in which the spectra of two orthogonal polarizations of transmitted light or reflected light are a bit different due to metal nanoparticles arranged in an anisotropic period in a metal nanoparticle layer of the test specimen. Thus a signal of phase difference with a quite narrow bandwidth is generated and can be measured by ellipsometry. Therefore the figure of merit of the sensing system is significantly improved.

Description of Related Art

The LSPR is a collective oscillation of free electrons in metal nanoparticles when excited by electromagnetic waves. The LSPR induces peaks or troughs in spectra of absorption, scattering, transmittance or reflectance at the resonance frequency. The resonance frequency of metal nanoparticles will shift due to delicate change of refractive index of the environment which can be caused by binding of molecules on nanoparticles or change of solution density of chemical substances, etc. Thus the refractive index changes can be learned by monitoring the spectral shift of resonance frequency. The LSPR technique with advantages of high sensitivity and real-time detection has been widely used in chemical and biological sensors. The sensitivity of sensor is defined as the spectral shift divided by a refractive index change. In addition to the sensitivity, the capability of sensor is also concerned with the full width at half maximum (FWHM) of the peak/trough. A figure of merit (FOM) defined as the sensitivity divided by the FWHM is widely used to characterize the sensor performance. It can be expected that the sensor with narrower bandwidth has better quality/performance among sensors with the same sensitivity.

The LSPR sensors offer small FOM typically ranging from 1 to 2 owing to the broad line shape of LSPR. In recent years, many methods for restraining the FWHM to improve the FOM have been proposed. Leif J. Sherry et al. (Nano Lett. 5, 2034 (2005)) observed a higher order mode of nanocubes excited by the contact of the substrate. The mode possesses a FWHM narrower than the dipole mode, and thus resulting in a higher FOM. Peter Offermans et al. (ACS Nano 5, 5151 (2011)) demonstrated an enhanced FOM of sensor of periodic arranged nanoparticles. The coupling of Wood-Rayleigh anomaly and the LSPR restrains the FWHM of the sensor. Currently, most of the proposed methods are based on detection of light intensity. However, according to the research of Andrei V. Kabashin et al. (Opt. Express 17, 21191 (2009)), phase detection algorithms with the advantages of higher signal-to-noise ratios and better sensitivities give the possibility to achieve lower detection limits.

A novel phase detection algorithm with wavelength interrogation is proposed by Kristof Lodewijks et al. (Nano Lett. 12, 1655 (2012)). They designed test specimen which are composed of a gold thin film, a dielectric layer and a nanoparticle layer. In the instrument, the resonant frequency of S polarization and P polarization is separated by oblique incidence and thus a phase difference is generated between the two polarization states. The bandwidth of the phase signal measured by ellipsometry is narrower than the bandwidth of the reflectance so that the FOM is increased 6.1 times. However, the fabrication process of the test specimens is more complicated than general LSPR test specimen due to the additional gold thin film and the dielectric layer disposed under the nanoparticle layer. Thus the manufacturing cost is increased. Moreover, its optical path is incident obliquely and is achieved by a rotary arm or more complicated optical design. The above shortcomings hinder the commercialization of the technique. Thus there is room for improvement and a need to provide a novel LSPR sensing system that overcomes the above shortcomings.

SUMMARY

Therefore it is a primary object of the present invention to provide a LSPR sensing system with particles arranged in an anisotropic period in which the spectra of two orthogonal polarization states of transmitted light or reflected light are slightly split in spectra due to anisotropic arrangement of nanoparticles in a metal nanoparticle layer. Thus a phase difference with a quite narrow bandwidth is generated between two orthogonal polarization states of the emergent light so as to increase the FOM of the sensing system dramatically. The embodiments according to the present invention enable the use of test specimens of one layer metal structure and the setup of a simple optical path in normal incidence. Therefore the present invention overcomes the shortcomings of the prior art.

In order to achieve the above object, a LSPR sensing system with particles arranged in an anisotropic periodic manner is revealed. The system features on that a phase signal of LSPR is generated by metal nanoparticles arranged anisotropically and the sensing is accomplished by measuring the spectral position of the phase signal. The system of the present invention includes at least one light source generating an incident light, a polarizer for polarizing the incident light, a test specimen, an analyzer that filters out the polarization state of an emergent light passing through the test specimen, a monochromator disposed on a light path of the system and used to acquire the spectral information, and an optical detection system that receives light emerging from the test specimen and detects spectrum of a phase signal of the emergent light.

The above test specimen includes a metal nanoparticle layer formed by a plurality of metal nanoparticles arranged thereon periodically. The periodic arrangement doesn't have 4-fold rotational symmetry (90 degrees), in other words, the nanoparticle layer is anisotropic. The metal nanoparticle layer is in contact with the analyte and is excited by the incident light to sustain the LSPR. Thereby the spectra of two perpendicular polarization states of transmitted light or reflected light are slightly split away from each other due to anisotropic periodic arrangement of the metal nanoparticles on the metal nanoparticle layer. Being measured by ellipsometry, it is found that a signal with quite narrow bandwidth is generated in the phase difference spectrum. The FWHM of the phase difference spectrum is narrower than the FWHM obtained by measuring the transmittance or reflectance. Therefore the FOM is dramatically increased and the performance of the refractive index sensor is hence improved.

The metal nanoparticle is made from metals including gold, silver, copper, aluminum, palladium, platinum, tin, white gold, etc. Moreover, the shape of the metal nanoparticle can be a square, a circle, a rectangle, or an ellipse. When the arrangement of the nanoparticles is a rectangle array, the preferred length of the period along the X axis and the period thereof along the Y axis match the requirement of: 1>the length of the short side/the length of the long side >0.8. In an apparatus of the present invention, the layer of nanoparticles can be a porous layer of nanoholes.

The light is multichromatic to enable the spectral measurement and the light emerging from the test specimen can be transmitted light or reflected light. A preferred setup of optical path is to detect the transmitted light from the specimen under normal incidence, and hence the optical path is simple to implement and there is no need to use a rotary arm.

The light output from the test specimen is a superposition of two orthogonal polarization states. The phase signal the optical detection system measured is a difference between phases of the two orthogonal polarization states. The present system detects changes of environmental refractive index by the spectral shift in the phase difference spectrum. The spectral shift of the present system can be indicated as wavelength change, frequency change and photon energy change.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION

LSPR is a collective oscillation of free electrons in metallic nanostructures. The excitation of LSPRs results in characteristic peaks and troughs in spectra of transmittance and reluctance. In addition, the phase of the transmittance and reflectance would be manipulated by the LSPR thus resulting in optical phenomena such as steep phase transition and phase retardation. The phase variations of LSPR are possible to be measured using ellipsometry. The main optical components of the ellipsometer include a light source, a polarizer, an analyzer, a monochromator, and a detector. The use of compensators in the optical path of ellipsometer is optional, depending on the applications. An ellipsometer measures the complex ratio between two perpendicular components of electric field of light such as $E_x$ and $E_y$. That is $$T = \frac{E_y}{E_x} = \tan(\psi)e^{i\Delta}$$

where, $\tau$ is the amplitude ratio and $\Delta$ is the phase difference.

Figure 1:
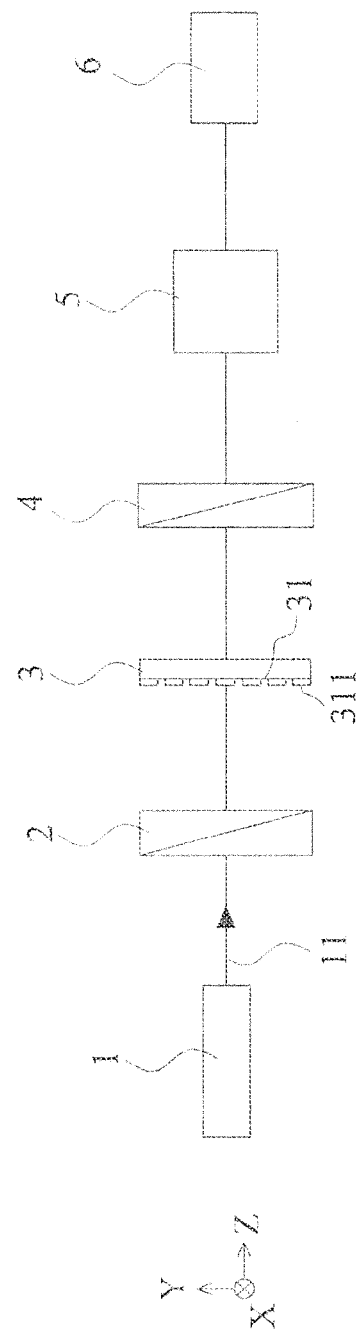
FIG. 1 is a schematic drawing showing structure of an embodiment of a LSPR sensing system according to the present invention.

Refer to FIG. 1, a block diagram of an embodiment of a LSPR sensing system according to the present invention is revealed. The system features on that a phase signal of LSPR is generated by metal nanoparticles 311 arranged in an anisotropic manner and the spectral shift of the phase signal is monitored by ellipsometry to detect the change of the environment of nanoparticles. The LSPR sensing system of the present invention includes a light source 1, a polarizer 2, a test specimen 3, an analyzer 4, a monochromator 5, and an optical detection system 6.

The light source 1 is used for generating an incident light 11. The light generated is not a monochromatic light. The bandwidth of the light is narrowed and the center wavelength is selected in the optical path by the monochromator 5 for generating the spectra.

The polarizer 2 is for polarizing the above incident light 11.

Figure 2:
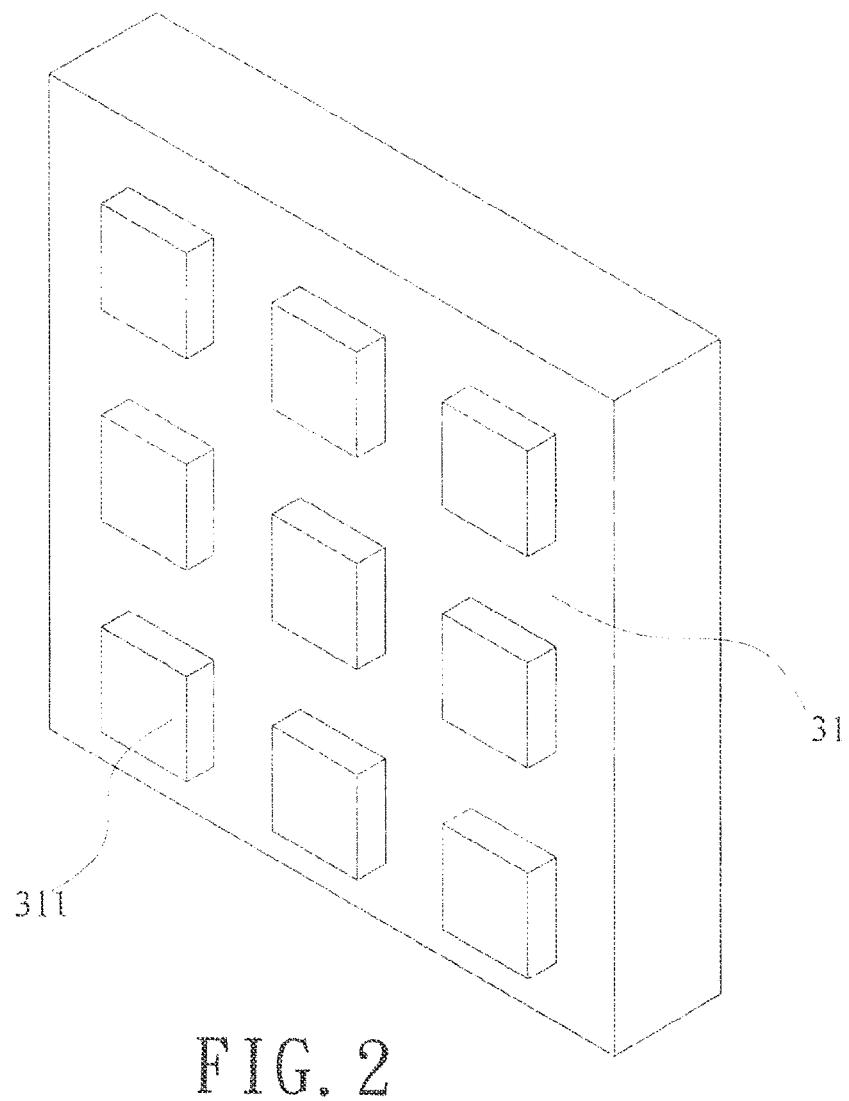
FIG. 2 is a schematic drawing showing a periodic arrangement of metal nanoparticles on a metal nanoparticle layer of an embodiment and the periodic arrangement doesn't have 4-fold rotational symmetry (90 degrees) according to the present invention.
Figure 3:
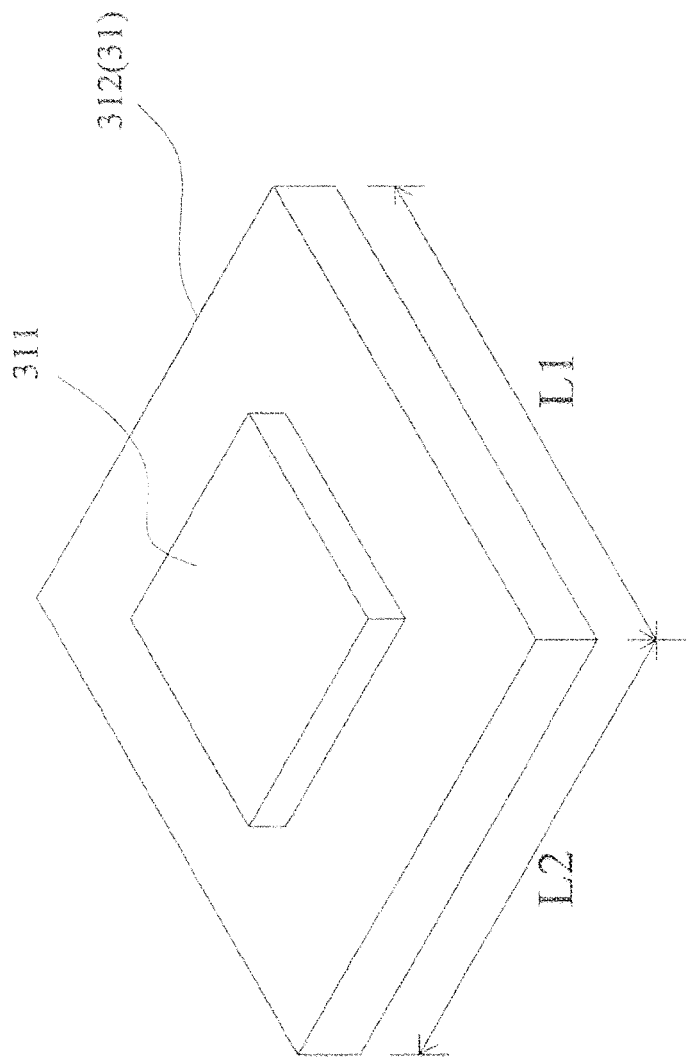
FIG. 3 is a schematic drawing showing a unit of a metal nanoparticle layer of an embodiment according to the present invention.
Figure 3:
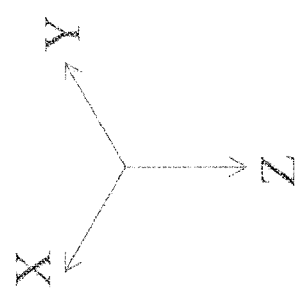

The test specimen 3 includes a metal nanoparticle layer 31 formed by a plurality of metal nanoparticles 311 that is made from gold, silver, copper, aluminum, palladium, platinum, tin, white gold, etc. Refer to FIG. 2, a schematic drawing showing an embodiment of a metal nanoparticle is disclosed. The periodic arrangement of the metal nanoparticles 311 in the metal nanoparticle layer 31 doesn't have 4-fold rotational symmetry. The metal nanoparticle layer 31 includes a plurality of units 312, as shown in FIG. 3. The length of the side of the unit 312 along the Y-axis is defined as a long side (L1) of the unit 312 while the length of the side of the unit 312 along the X-axis is defined as a short side (L2) of the unit 312. The long side (L1) is not equal to the short side (L2). The preferred ratio between the short side (L2) of the unit and the long side (L1) of the unit meets a requirement of 1>a length of a short side (L2)/a length of a long side (L1)>0.8. The shape of the nanoparticle 311 is not limited; it can be a circle, a ellipse, a rectangle, etc. In this preferred embodiment, the shape of nanoparticle 311 is square. The metal nanoparticle layer 31 is in contact with analytes and is excited by the incident light 11 so as to sustain LSPR.

The analyzer 4 is used to filter out the polarization state of the emergent light after it passes through the test specimen 3. The emergent light from the test specimen 3 is either transmitted light or reflected light. In this embodiment, its transmitted light.

The monochromator 5 is arranged at a light path of the LSPR sensing system and used for resolving the wavelength of light to generate spectrum. In this embodiment, the monochromator 5 is arranged behind the analyzer 4, but not limited to this position. The monochromator 5 can be disposed on the light path the present system passes such as the position between the light generator 1 and the polarizer 2 or the position between the polarizer 2 and the test specimen 3. As long as the monochromator 5 provides the same effect, the position of the monochromator 5 is not limited.

The optical detection system 6 is for receiving the light emergent from the test specimen 3 and detecting the phase signal spectrum of the emergent light. The emergent light from the test specimen 3 is a superposition of two orthogonal polarization states of the light. Thus the phase signal the optical detection system 6 measured is a difference between phases of the two orthogonal polarizations. The phase signal has a spectral shift when the refractive index of the environment around the nanoparticles changes. The present system detects the change of environmental refractive index by monitoring the spectral shift. The spectral shift of the phase signal can be represented as one of the follows: wavelength change, frequency change and photon energy change.

In accordance with the above description, in the LSPR sensing system, the test specimen 3 is formed by a layer of silver square nanoparticles 31 deposited on a glass substrate. The metal nanoparticle layer 31 is considered to be formed by a plurality of units 312. Each unit 312 includes one metal nanoparticle 311. As shown in FIG. 3, the length of the metal nanoparticle 311 along the X axis and the length thereof along the Y axis are both 250 nm and the environmental refractive index is 1.33. The length of the short side of the unit 312 (L2) is 500 nm while the length of the long side of the unit 312 (L1) is 550 nm. To present the function of the embodiment, the spectra of X and Y polarizations of light passing through the test specimen 3 are given by rigorous coupled wave analysis.

While in use, the simulated phase spectrum of Y polarization ( . . . dotted line in FIG. 4) is shifted to a shorter wavelength, relative to the simulated phase spectrum of X polarization (- solid line), due to the metal nanoparticles 311 of the metal nanoparticle layer 31 arranged in the anisotropic periodic manner on surface of the test specimen 3. The phase spectra of X and Y polarizations show steep variations at around 1050 nm wavelength, which are phase transitions induced by the LSPRs. Because of the phase transition phenomenon, a small spectral shift results in an enormous difference between the phases of X and Y polarizations.

Figure 4:
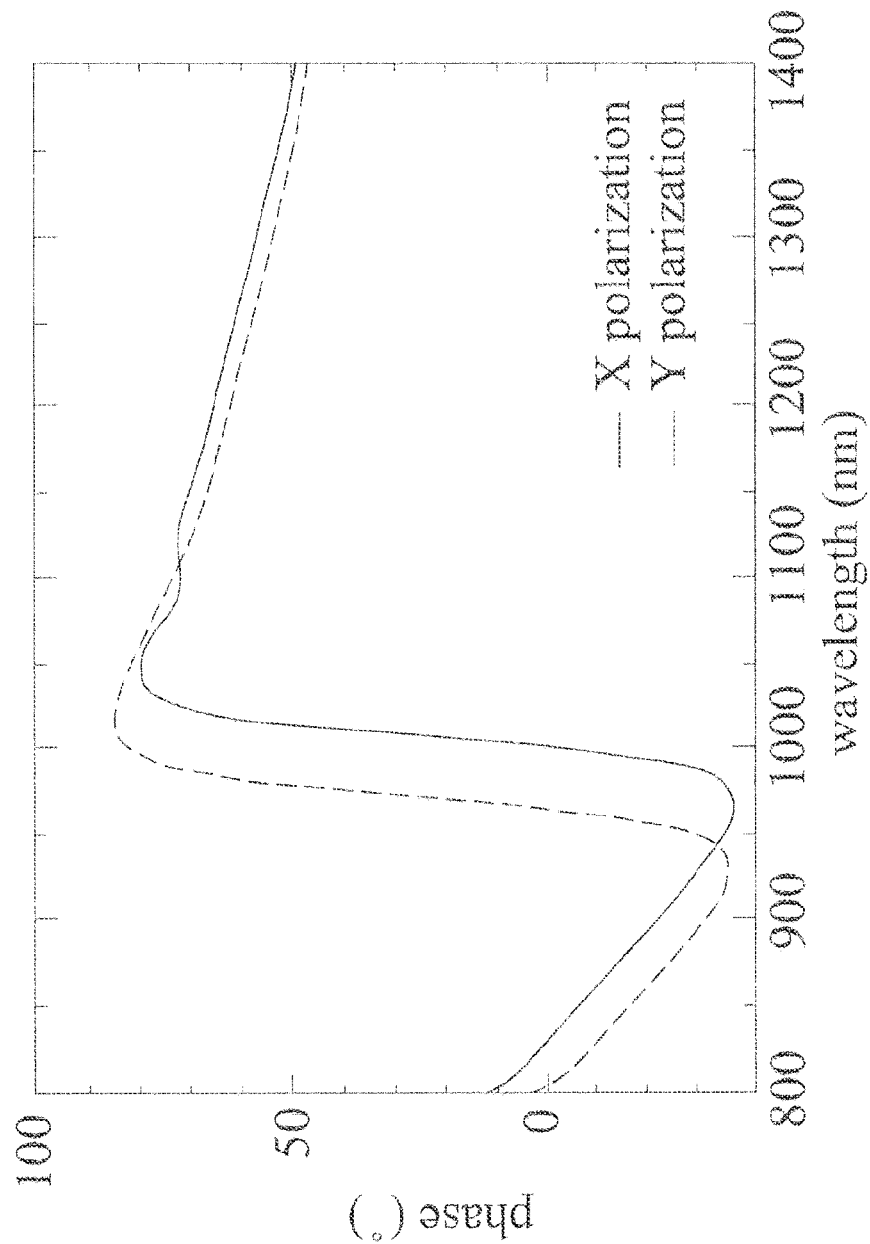
FIG. 4 is a diagram showing simulated phases of X and Y polarization states of light passing through a test specimen as functions of wavelength in an embodiment according to the present invention.
Figure 5:
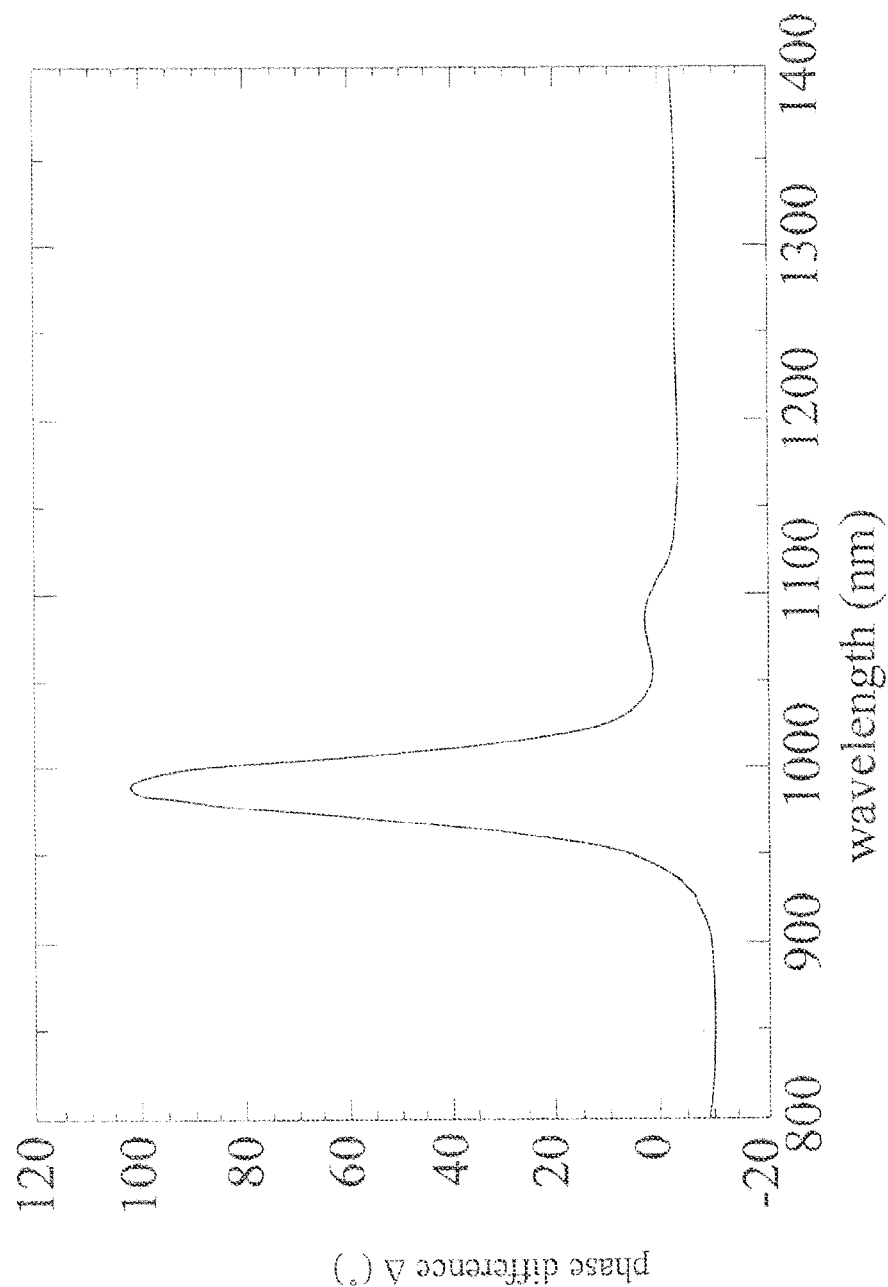
FIG. 5 is a diagram showing the phase difference between X and Y polarization states of light passing through a test specimen as a function of wavelength in an embodiment according to the present invention.
Figure 6:
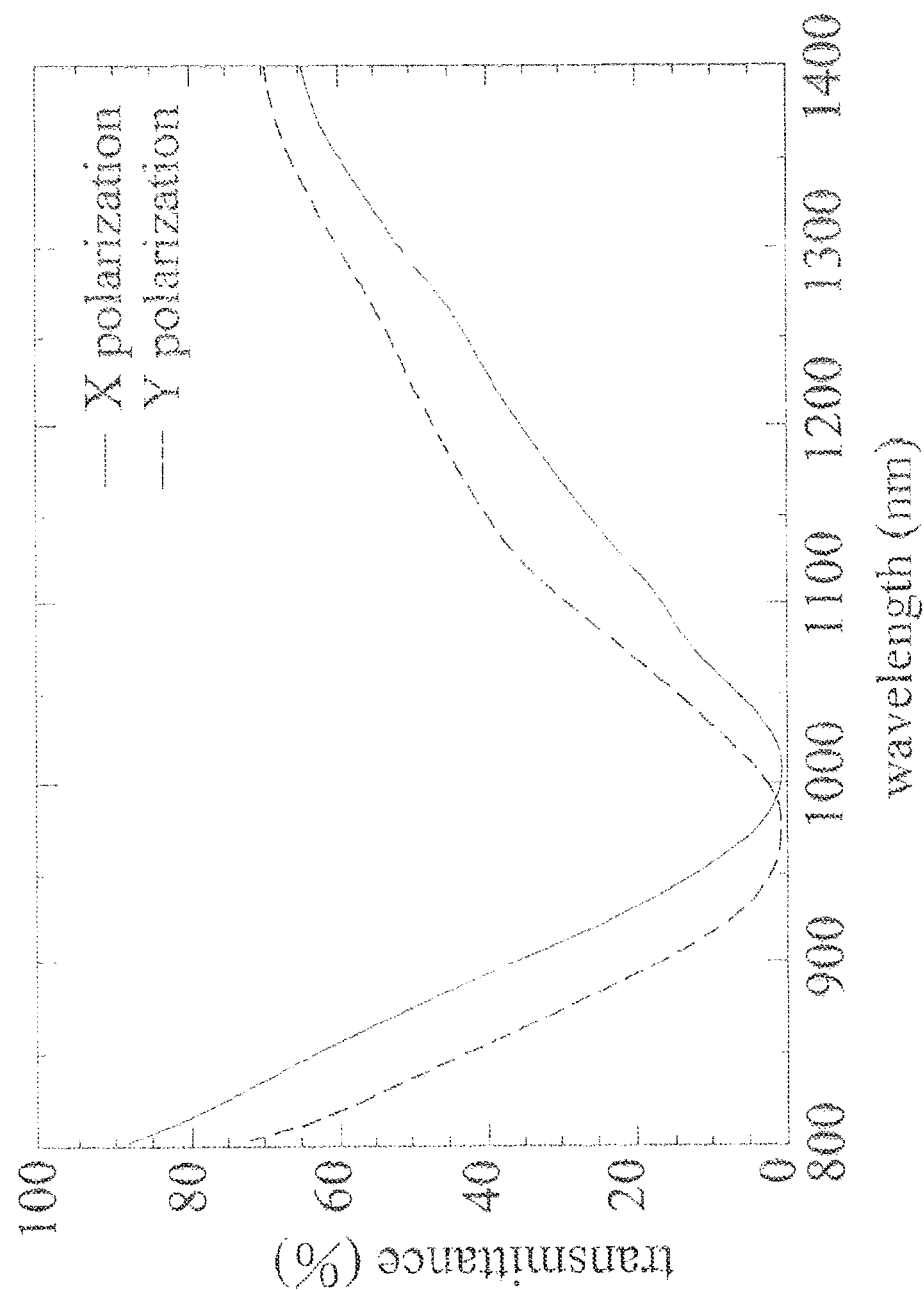
FIG. 6 is a diagram showing the simulated transmittances of X and Y polarizations as functions of wavelength in an embodiment according to the present invention.

Also refer to FIG. 5, the phase difference Δ is the difference between the phase of the X polarization and that of the Y polarization shown in FIG. 4. In practice, the phase difference can be measured by the system of ellipsometer revealed in FIG. 1. There is a signal with a very narrow bandwidth in the spectrum of the phase difference and its FWHM is 39.7 nm. Refer to FIG. 6, the simulated transmittances of the X and Y polarizations are disclosed. The FWHM of the X polarized light and that of the Y polarized light are respectively 394 nm and 379 nm. The FWHM of the phase difference spectrum is much narrower than the FWHMs of the transmittances measured. Thus the FOM of the sensing system is significantly increased.

Figure 7:
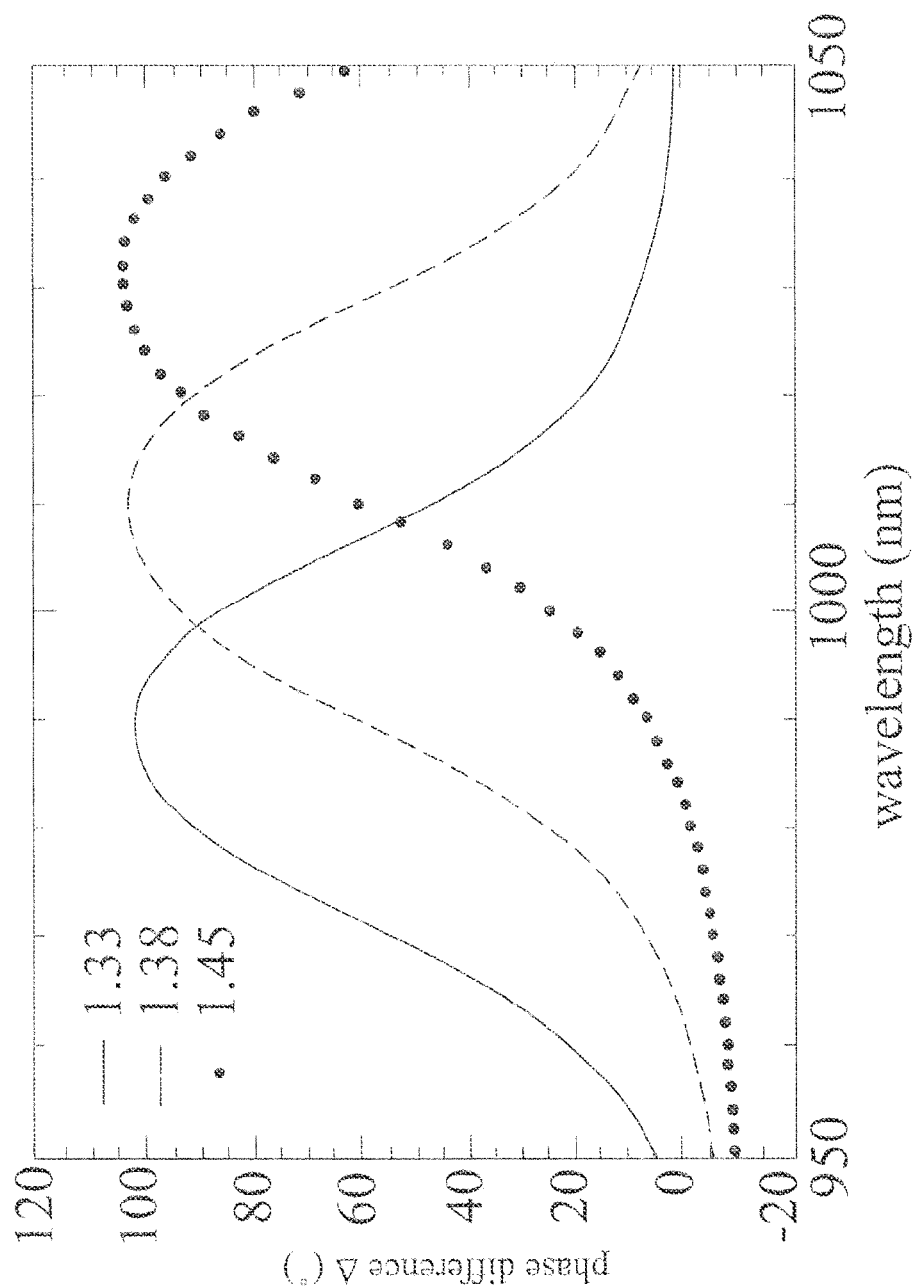
FIG. 7 is a diagram showing the phase differences .DELTA. for nanoparticles in test specimen embedded in different environments with refractive indices of 1.33, 1.38, and 1.43.

Refer to FIG. 7, the phase differences Δ for nanoparticles 311 in test specimen 3 embedded in different environments with refractive indices of 1.33 (- solid line), 1.38 ( - - - dash line), and 1.43 ( . . . dotted line) is shown. The spectral position of phase difference Δ is red shifted with the increase of environmental refractive index. The presented embodiment of LSPR sensing system monitors the spectral shift of phase difference Δ while the test specimen 3 is in contact with analyte. The spectral shift of phase difference Δ indicates the variation of the environmental refractive index.

Figure 8:
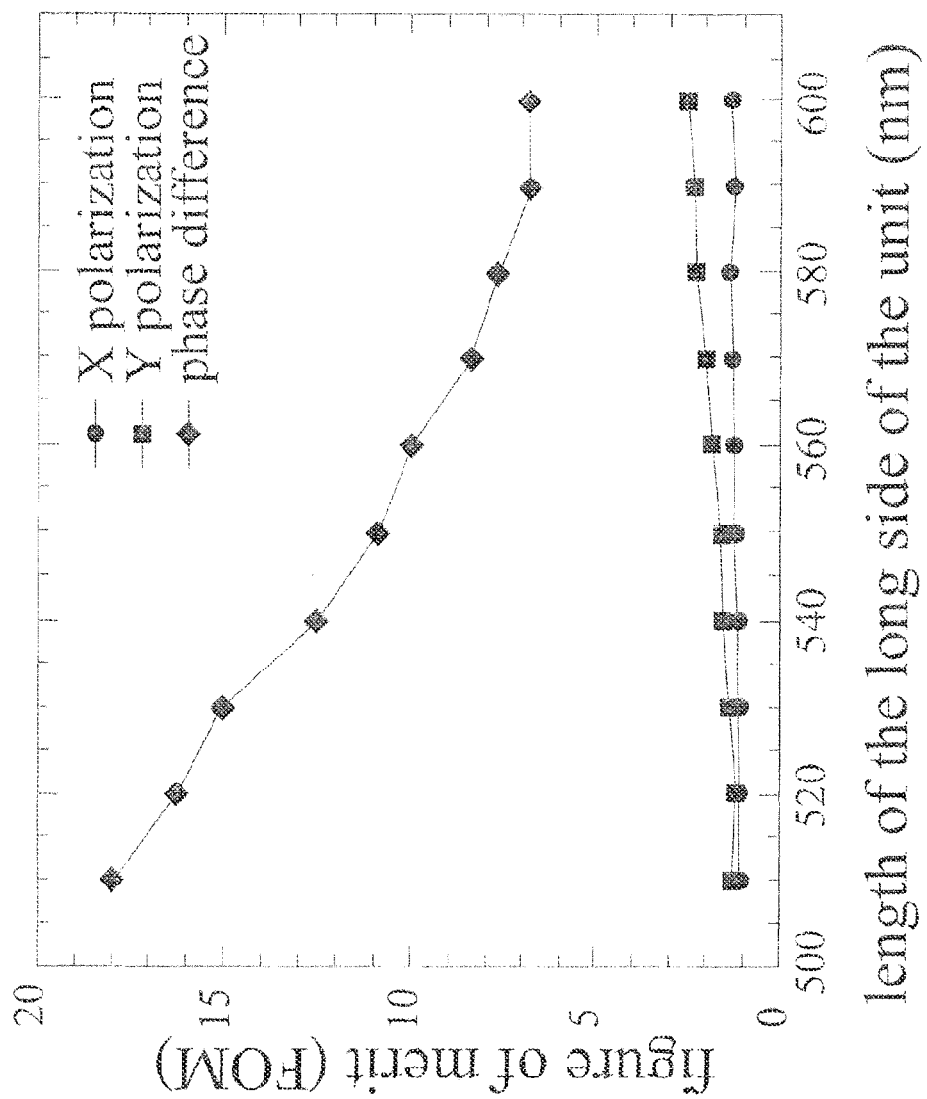
FIG. 8 is a diagram showing a relationship between simulated FOMs of X polarization, Y polarization, and phase difference, and a length of a long side of a unit of an embodiment according to the present invention.

Refer to FIG. 8, a diagram showing relationship between the length of the long side (L1) of the unit 312 and the simulated FOMs of X polarization, Y polarization, and phase difference Δ is revealed. The length of the short side (L2) of the unit 312 is 500 nm; and the length of the long side (L1) of the unit 312 is varied from 510 nm to 600 nm. In FIG. 8, the FOM of phase difference (-♦- diamond dots) is much higher than the FOM of X polarization (-●- circle dots) and the FOM of Y polarization (-■- square dots). FOM of phase difference is about 10 when the length of the short side (L2) of the unit/the length of the long side (L1) of the unit is equal to 0.91 while the length of the long side (L1) of the unit is 550 nm. As the length of the long side (L1) further approaches 510 nm, the FOM increases to exceeding 10.

Figure 9:
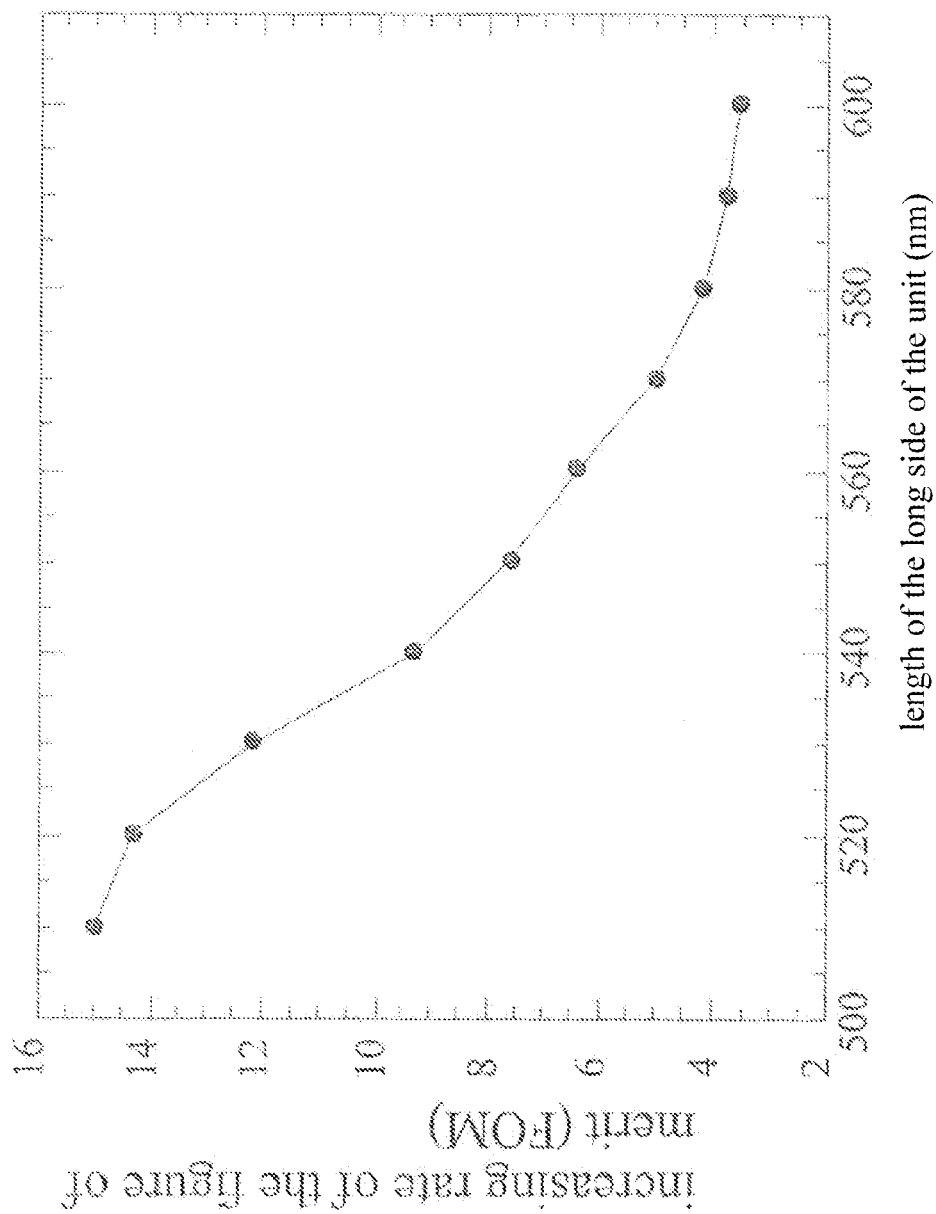
FIG. 9 is a diagram showing a relationship between FOM increase ratio and a length of a long side of a unit of an embodiment according to the present invention.

Refer to FIG. 9, a diagram showing relationship between the length of the long side (L1) of the unit and the FOM increase ratio is revealed. The FOM increase ratio is defined as FOM of the phase difference divided by average FOM of X and Y polarizations. It can be learned in FIG. 8 and FIG. 9 that FOM is 16.2 and FOM increase ratio is 14.3 when the length of the long side (L1) of the unit 312 is 520 nm. When the length of the long side (L1) of the unit 312 is 510 nm, the FOM is 18.0 and the FOM increase ratio is 15.0.

The results show that the LSPR sensing system with nanoparticles arranged in an anisotropic periodic manner according to the present invention greatly enhanced the value of FOM. In addition, phase sensing technology promises a signal-to-noise ratio higher than the intensity sensing technology. The present invention is expected to obtain a lower detection limit relative to the technology of intensity sensing. Compared with the invention proposed by Kristof Lodewijks et al. (Nano Lett. 12, 1655 (2012)), there is no need to fabricate the test specimen with complicated multilayer structure, thus lowering the cost of the test specimen. Moreover, the optical path is in normal incidence so that the rotary arm is not required and the optical design is simple. It should be noted that the rectangle shape of the metal nanoparticle 311 is only a preferred embodiment of the present invention. The shape of metal nanoparticle 311 is not limited. The arrangement of the metal nanoparticles 311 is also not limited to a rectangular array. They can be arranged into a hexagonal array. Moreover, the metal nanoparticles 311 which form the metal nanoparticle layer 31 are only an embodiment of the present invention. The metal nanoparticle layer 31 can also be a porous structure of nanoholes with a similar effect and technical advantages as the above embodiment.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for a localized surface plasmon resonance (LSPR) sensing system having an optical detection system and a test specimen with a plurality of metal nanoparticles arranged in an anisotropic periodic manner that generates a phase signal of the LSPR sensing system, the method comprising:
   emitting an incident light toward the test specimen to excite the metal nanoparticles, thereby generating an emergent light;
   using the optical detection system to detect phases of a first polarization state and a second polarization state of the emergent light, wherein the first polarization state is perpendicular to the second polarization state;
   obtaining a phase difference spectrum between the phases of the first and second polarization states, thereby determining a half maximum (FWHM) of the phase difference spectrum; and
   monitoring a spectral shift of the phase signal to detect a change of an environment refractive index associated with the metal nanoparticles.

2. The method as claimed in claim 1, wherein the test specimen is used having a plurality of units adjacent to each other and respectively having the metal nanoparticles, wherein each of the units has a long side and a short side perpendicular to each other, and in each of the units, the length of the short side is different from the length of the long side, and the ratio of the length of the short side to the length of the long side is between 0.8 and 1.

3. The method as claimed in claim 1, further comprising:
   using a polarizer to polarize the incident light; and
   using an analyzer to filter out the first and second polarization states of the emergent light.

4. The method as claimed in claim 3, further comprising:
   using a monochromator to narrow a bandwidth of the emergent light after the emergent light passes through the analyzer.

5. The method as claimed in claim 3, further comprising:
   using a monochromator to narrow a bandwidth of the incident light before the incident light passes through the polarizer.

6. The method as claimed in claim 1, wherein the incident light is not a monochromatic light.

7. The method as claimed in claim 1, wherein the emergent light is a transmitted light penetrating through the test specimen.

8. The method as claimed in claim 1, wherein the emergent light is a reflected light reflected by the test specimen.

9. The method as claimed in claim 1, further comprising:
   using the optical detection system to detect the phase signal, wherein the phase signal is a difference between the phases of the first and second polarization states.

10. The method as claimed in claim 1, wherein the spectral shift of the phase signal is used representing as one of a wavelength change, a frequency change and a photon energy change.

11. The method as claimed in claim 1, wherein material of the metal nanoparticles is selected from the group consisting of gold, silver, copper, aluminum, palladium, platinum, tin, and white gold.

12. The method as claimed in claim 1, wherein the metal nanoparticles are in a shape having 4-fold rotational symmetry (90 degrees).

13. The method as claimed in claim 1, wherein the metal nanoparticles are in a shape not having 4-fold rotational symmetry (90 degrees).

14. The method as claimed in claim 1, wherein the metal nanoparticles are in a shape of rectangle or ellipse.

15. The method as claimed in claim 1, wherein the metal nanoparticles are in a shape of circle or square.

* * * * *